(12) United States Patent
Harats et al.

(10) Patent No.: US 7,585,666 B2
(45) Date of Patent: *Sep. 8, 2009

(54) POLYNUCLEOTIDE CONSTRUCTS, PHARMACEUTICAL COMPOSITIONS AND METHODS FOR TARGETED DOWNREGULATION OF ANGIOGENESIS AND ANTICANCER THERAPY

(75) Inventors: Dror Harats, Ramat Gan (IL); Shoshana Greenberger, Petach Tikva (IL); Eyal Breitbart, Hashmonaim (IL)

(73) Assignee: Vascular Biogenics Ltd., Or Yehuda (IL)

( * ) Notice: Subject to any disclaimer, the term of this patent is extended or adjusted under 35 U.S.C. 154(b) by 383 days.

This patent is subject to a terminal disclaimer.

(21) Appl. No.: 10/490,746

(22) PCT Filed: May 1, 2002

(86) PCT No.: PCT/IL02/00339

§ 371 (c)(1),
(2), (4) Date: Apr. 12, 2004

(87) PCT Pub. No.: WO03/033514

PCT Pub. Date: Apr. 24, 2003

(65) Prior Publication Data

US 2004/0197860 A1 Oct. 7, 2004

Related U.S. Application Data

(60) Provisional application No. 60/330,118, filed on Oct. 19, 2001.

(51) Int. Cl.
C12N 15/00 (2006.01)
C12N 5/00 (2006.01)
C12N 5/02 (2006.01)

(52) U.S. Cl. .................... 435/320.1; 435/455; 435/325; 536/23.1

(58) Field of Classification Search ................. 435/455, 435/320.1, 325; 536/23.1
See application file for complete search history.

(56) References Cited

U.S. PATENT DOCUMENTS

| | | | |
|---|---|---|---|
| 4,866,042 A | 9/1989 | Neuwelt | |
| 5,464,764 A | 11/1995 | Capecchi et al. | |
| 5,635,385 A | 6/1997 | Leopold et al. | |
| 5,686,281 A * | 11/1997 | Roberts ...................... 435/456 | |
| 5,734,039 A | 3/1998 | Calabretta et al. | |
| 5,747,340 A * | 5/1998 | Harats et al. ................ 435/456 | |
| 5,792,453 A | 8/1998 | Hammond et al. | |
| 5,830,880 A * | 11/1998 | Sedlacek et al. .............. 514/44 | |
| 5,906,827 A | 5/1999 | Khouri et al. | |
| 5,916,763 A | 6/1999 | Williams et al. | |
| 6,027,743 A | 2/2000 | Khouri et al. | |
| 6,110,480 A | 8/2000 | Chu et al. | |
| 6,180,355 B1 | 1/2001 | Alexander et al. | |
| 6,183,737 B1 | 2/2001 | Zaleske et al. | |
| 6,200,751 B1 | 3/2001 | Gu et al. | |
| 6,206,917 B1 | 3/2001 | Williams et al. | |
| 6,239,151 B1 | 5/2001 | Broadhurst et al. | |
| 6,265,216 B1 | 7/2001 | Bennett et al. | |
| 6,300,127 B1 | 10/2001 | Hair et al. | |
| 6,300,490 B1 | 10/2001 | Huber et al. | |
| 6,376,244 B1 | 4/2002 | Atala | |
| 6,438,802 B1 | 8/2002 | Beeman et al. | |
| 6,444,803 B1 | 9/2002 | Hair et al. | |
| 6,479,064 B1 | 11/2002 | Atala | |
| 6,497,725 B2 | 12/2002 | Williams et al. | |
| 6,521,750 B2 | 2/2003 | Hair et al. | |
| 6,576,265 B1 | 6/2003 | Spievack | |
| 6,579,697 B1 * | 6/2003 | Wallach et al. ............. 435/69.1 | |
| 6,627,189 B1 | 9/2003 | Roth et al. | |
| 6,652,583 B2 | 11/2003 | Hopkins et al. | |
| 6,783,776 B2 | 8/2004 | Spievack | |
| 7,067,649 B2 | 6/2006 | Harats | |
| 2003/0124100 A1 | 7/2003 | Harats | |
| 2004/0048280 A1 | 3/2004 | Harats | |
| 2004/0224389 A1 * | 11/2004 | Bellgrau et al. ............. 435/69.1 | |
| 2005/0112110 A1 | 5/2005 | Harats | |

(Continued)

FOREIGN PATENT DOCUMENTS

WO       WO 98/00013        1/1998

(Continued)

OTHER PUBLICATIONS

Varda-Bloom, et al. Tissue-Specific Gene Therapy Directed to Tumor Angiogenesis, Gene Therapy 8:819-827, 2001.*

(Continued)

Primary Examiner—Thaian N Ton

(57) ABSTRACT

A novel nucleic acid construct for down-regulating angiogenesis in a tissue of a subject is provided. The nucleic acid construct includes: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in a specific tissue or cell; wherein the ligand binding domain is selected such that it is capable of binding a ligand present in the specific tissue or cell, whereas binding of the ligand to the ligand binding domain activates the effector domain of the apoptosis signaling molecule. Also provided are methods of utilizing this nucleic acid construct for treating diseases characterized by excessive or aberrant neo-vascularization or cell growth.

5 Claims, 9 Drawing Sheets

U.S. PATENT DOCUMENTS

| | | |
|---|---|---|
| 2005/0186179 A1 | 8/2005 | Harats et al. |
| 2006/0204478 A1 | 9/2006 | Harats et al. |
| 2007/0286845 A1 | 12/2007 | Harats et al. |

FOREIGN PATENT DOCUMENTS

| | | |
|---|---|---|
| WO | WO 98/37901 | 9/1998 |
| WO | WO 00/06759 | 2/2000 |
| WO | WO 02/40629 | 5/2002 |
| WO | WO 03/033514 | 4/2003 |
| WO | WO 03/093409 | 11/2003 |
| WO | WO 2004/113497 | 12/2004 |
| WO | WO 2006/051545 | 5/2006 |
| WO | WO 2007/096882 | 8/2007 |
| WO | WO 2008/132729 | 11/2008 |

OTHER PUBLICATIONS

Greenberger, et al. Transcription-Controlled Gene Therapy Against Tumor Angiogenesis, The Journal of Clinical Investigation 113(7):1017-1024.*

Verma et al. (1997, Nature, vol. 389, pp. 239-242).*

Anderson et al.(1998, Nature, vol. 392, pp. 25-30).*

Palu et al.(1999, Journal of Biotechnology, vol. 68, pp. 1-13).*

Aird et al. "Human von Willebrand Factor Gene Sequences Target Expression to A Subpopulation of Endothelial Cells in Transgenic Mice", Proc. Natl. Acad. Sci. USA, 92: 4567-4571, 1995.

Aoki et al. "In Vivo Transfer Efficiency of Antisense Oligonucleotides Into the Myocardium Using HVJ-Liposome Method", Biochemical and Biophysical Research Communications, 231: 540-545, 1997.

Araki et al. "Ninjurin2, A Novel Homophilic Adhesion Molecule, Is Expressed in Mature Sensory and Enteric Neurons and Promotes Neurite Outgrowth", The Journal of Neuroscience, 20(1): 187-195, 2000.

Arap et al. "Cancer Treatment by Targeted Drug Delivery to Tumor Vasculature in A Mouse Model", Science, New Series, 279(5349): 377-380, 1998.

Ausprunk et al. "Migration and Proliferation of Endothelial Cells in Preformed and Newly Formed Blood Vessels During Tumor Angiogenesis", Microvascular Research, 14: 53-65, 1977.

Barcelos et al. "Impaired Inflammatory Angiogenesis, But Not Leukocyte Influx, in Mice Lacking TNFR1", Journal of Leukocyte Biology, 78: 352-358, Aug. 2005.

Bobek et al. "Gene Therapy of the Ischemic Lower Limb—Therapeutic Angiogenesis", Vascular Pharmacology, 44: 395-405, 2006.

Boldin et al. "A Novel Protein That Interacts With the Death Domain of Fas/APO1 Contains A Sequence Motif Related to the Death Domain", The Journal of Biological Chemistry, 270(14): 7795-7798, 1995.

Brown et al. "Neovascularisation and Its Role in the Osteoarthritic Process", Annals of the Rheumatic Diseases, 47: 881-885, 1988.

Bu et al. "Identification of An Endothelial Cell-Specific Regulatory Region in the Murine Endothelin-1 Gene", Journal of Biological Chemistry, 272(51): 32613-32622, 1997.

Carmeliet et al. "Growing Better Blood Vessels", Nature Biotechnology, 19: 1019-1020, 2001.

Chen et al. "Upstream Stimulatory Factors Regulate Aortic Preferentially Expressed Gene-1 Expression in Vascular Smooth Muscle Cells", The Journal of Biological Chemistry, 276(50): 47658-47663, 2001.

Cho et al. " Development of an Efficient Endothelial Cell Specific Vector Using Promoter and 5' Untranslated Sequences From the Human Proproendothelin-1 Gene", Experimental and Molecular Medicine, 35(4): 269-274, 2003.

Collins et al. "Molecular Cloning of the Human Gene for Von Willebrand Factor and Identification of the Trascription Initiation Site". Proc. Natl. Acad. Sci. USA, 84: 4393-4397, 1987.

Collins et al. "Structure and Chromosomal Location of the Gene for Endothelial-Leukocyte Adhesion Molecule 1", The Journal of Biological Chemistry, 266(4): 2466-2473, 1991.

Dor et al. "Induction of Vascular Networks in Adult Organs: Implications to Proangiogenic Therapy", Annals of the NY Academy of Sciences, 995: 208-216, 2003.

Edelberg et al. "Platelet-Derived Growth Factor-AB Limits the Extent of Myocardial Infarction in A Rat Model: Feasibility of Restoring Impaired Angiogenic Capacity in the Aging Heart", Circulation, 105: 608-613, 2002.

Epstein et al. "Therapeutic Interventions for Enhancing Collateral Development by Administration of Growth Factors: Basic Principles, Early Results and Potential Hazards", Cardiovascular Research, 49: 532-542, 2001.

Faries et al. "Assessing the Role of Gene Therapy in the Treatment of Vascular Disease", Annals of Vascular Surgery, 14(2): 181-188, 2000.

Feldman et al. "Progress in Antiangiogenic Gene Therapy of Cancer", Cancer, 89: 1181-1194, 2000.

Folkman "How Is Blood Vessel Growth Regulated in Normal and Neoplastic Tissue?—G.H.A. Clowes Memorial Award Lecture", Cancer Research, 46: 467-473, 1986.

Garlanda et al. "Heterogeneity of Endothelial Cells . Specific Markers", Arteriosclerosis, Thrombosis, and Vascular Biology, 17(7): 1193-1202, 1997.

Goldman et al. "Influence of Pressure on Permeability of Normal and Diseased Muscular Arteries to Horeseradish Peroxidase. A New Catheter Approach", Atherosclerosis, 65: 215-225, 1987.

Gorski et al. "Potentiation of the Antitumor Effect of Ionizing Radiation by Brief Concomitant Exposures to Angiostatin", Cancer Research, 58: 5686-5689, 1998.

Gu et al. "HTERT Promoter Induces Tumor-Specific Bax Gene Expression and Cell Killing in Syngenic Mouse Tumor Model and Prevents Systemic Toxicity", Gene Therapy, 9:30-37, 2002.

Harada et al. "Basic Fibroblast Growth Factor Improves Myocardial Function in Chronically Ischemic Porcine Hearts", Journal of Clinical Investigation, 94: 623-630, 1994.

Harats et al. "Targeting Gene Expression to the Vascular Wall in Transgenic Mice Using the Murine Preproendothelin-1 Promoter", Journal of Clinical Investigation, 95(3): 1335-1344, 1994. p. 1336, Fig. 1.

Hoefer et al. "Direct Evidence for Tumor Necrosis Factor-αSignaling in Arteriogenesis", Circulation, 105: 1639-1641, Apr. 9, 2002.

Iris et al. "Dense Alu Clustering and A Potential New Member of the NFκB Family Within A 90 Kilobase HLA Class III Segment", Nature Genetics, 3: 134-145, 1993.

Jäger et al. "Endothelial Cell-Specific Transcriptional Targeting From A Hybrid Long Terminal Repeat Retrovirus Vector Containing Human Prepro-Endothelin-1 Promoter Sequences", Journal of Virology, 73(12): 9702-9709, 1999.

Jones et al. "A Portable Regulatory Element Directs Specific Expression of the Caenorhabditis Elegans Ubiquitin Gene UBQ-2 in the Somatic Gonad", Developmental Biology, 171: 60-72, 1995.

Joshi et al. "Endothelial Cells Adhere to the RGD Domain and the Fibrinogen-Like Terminal Knob of Tenascin", Journal of Cell Science, 106: 389-400, 1993.

Kaiser et al. "Platelet-Derived Growth Factor, Intimal Hyperplasia, and Ischemic Complications in Giant Cell Arteritis", Arthritis & Rheumatism, 41(4): 623-633, 1998.

Kaito et al. "Potentiation of the Activity of Bone Morphogenetic Protein-2 in Bone Regeneration by A PLA-PEG/Hydroxyapatite Composite", Biomaterials, 26: 73-79, 2005.

Khan et al. "Gene Therapy Progeress and Prospects: Therapeutic Angiogenesis for Limb and Myocardial Ischemia", Gene Therapy, 10: 285-291, 2003.

Kolesnick et al. "Radiation and Ceramide-Induced Apoptosis", Oncogene, 22: 5897-5906, 2003.

Kong et al. "Gene Therapy Strategies for Tumor Antiangiogenesis", Journal of the National Cancer Institute, 90(3): 273-286, 1998.

Korhonen et al. "Endothelial-Specific Gene Expression Directed by the TIE Gene Promoter In Vivo", Blood, 86(5): 1828-1835, 1995.

Koshikawa et al. "Therapeutic Efficacy of the Suicide Gene Driven by the Promoter of Vascular Endothelial Growth Factor Gene Against Hypoxic Tumor Cells", Cancer Research, 60(11): 2936-2941, 2000.

Koyama et al. "Migratory and Proliferative Effect of Platelet-Derived Growth Factor in Rabbit Retinal Endothelial Cells: Evidence of An Autocrine Pathway of Platelet-Derived Growth Factor", Journal of Cellular Physiology, 158: 1-6, 1994.

Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.

Lavigne et al. "Enhanced Antisense Inhibition of Human Immunodeficiency Virus Type 1 in Cell Cultures by DLS Delivery System", Biochemical and Biophysical Research Communications, 237: 566-571, 1997.

Layne et al. "Characterization of the Mouse Aortic Carboxypeptidase-Like Protein Promoter Reveals Activity in Differentiated and Dedifferentiatid Vascular Smooth Muscle Cells", Circulation Research, 90: 728-736, 2002.

Lee et al. "Functional Analysis of the Endothelin-1 Gene Promoter", Journal of Biological Chemistry, 265(18): 10446-10450, 1990. Fig. 1, wherein Nucleotides—124 to—118 Are Identical to SEQ ID No. 5.

Liu et al. "Restenosis After Coronary Angioplasty. Potential Biologic Determinants and Role of Intimal Hyperplasia", Circulation, 79: 1374-1387, 1989.

Lowe et al. "Osteopetrosis in Src-Deficient Mice Is Due to an Autonomous Defect of Osteoclasts", Proc. Natl. Acad. Sci. USA, 90: 4485-4489, 1993.

Luft "Making Sense Out of Antisense Oligodeoxynucleotide Delivery: Getting There Is Half the Fun", Journal of Molecular Medicine, 76: 75-76, 1998.

Lyden "Impaired Recruitment of Bone-Marrow-Derived Endothelial and Hematopoietic Precursor Cells Blocks Tumor Angiogenesis and Growth", Nature Medicine, 7(11): 1194-1201, 2001.

Micheau et al. "STAT-1-Independent Upregulation of FAD and Procaspase-3 and -8 in Cancer Cells Treated With Cytotoxic Drugs", Biochemical and Biophysical Research Communications, 256: 603-607, 1999.

Minchenko et al. "Regulation of Endothelin-1 Gene Expression in Human Microvascular Endothelial Cells by Hypoxia and Cobalt: Role of Hypoxia Responsive Element", Molecualr and Cellular Biochemistry, 208(1-2): 53-62, 2000. p. 57, l-h col., § 2, p. 57, r-h col., Last §, Fig.2.

Morishita et al. "A Novel Promoter for Vascular Endothelial Growth Factor Receptor (Flt-1) That Confers Endothelial-Specific Gene Expression", The Journal of Biological Chemistry, 270(46): 27948-27953, 1995.

Newman et al. "PECAM-1 (CD31) Cloning and Relation to Adhesion Molecules of the Immunoglobulin Gene Superfamily", Science, New Series, 247(4947): 1219-1222, 1990.

Nicklin et al. "Selective Targeting of Gene Transfer to Vascular Endothelial Cells by Use of Peptides Isolated by Phage Display", Circulation, 102: 231-237, 2000.

O'Reilly et al. "Endostatin: an Endogenous Inhibitor of Angiogenesis and Tumor Growth", Cell, 88: 277-285, 1997.

Ozawa et al. "Histologic Changes of Nonbiodegradable and Biodegradable Biomaterials Used to Repair Right Ventricular Heart Defects in Rats", The Journal of Thoracic and Cardiovascular Surgery, 124(6): 1157-1164, 2002.

Patan et al. "Intussusceptive Microvascular Growth in a Human Colon Adenocarcinoma Xenograft: A Novel Mechanism of Tumor Angiogenesis", Microvascular Research, 51: 260-272, 1996.

Peng et al. "The Use of the L-Plastin Promoter for Adnoviral-Mediated, Tumor-Specific Gene Expression in Ovarian and Bladder Cancer Cell Lines", Cancer Research, 61: 4405-4413, 2001.

Plump et al. "Severe Hypercholesterolemia and Atherosclerosis in Apolipoprotein E-Deficient Mice Created by Homologous Recombination in ES Cells", Cell, 71: 343-353, 1992.

Rajur et al. "Covalent Protein-Oligonucleotide Conjugates for Efficient Delivery of Antisense Molecules", Bioconjugate Chemistry, 8: 935-940, 1997.

Richardson et al. "Polymeric System for Dual Growth Factor Delivery", Nature Biotechnology, 19: 1029-1034, 2001.

Risau "Mechanisms of Angiogenesis", Nature, 386: 671-674, 1997.

Rius et al. "Cloning of the Promoter Region of Human Endoglin, the Target Gene for Hereditary Hemorrhagic Telangiectasia Type 1", Blood, 92(12): 4677-4690, 1998.

Sano et al. "Functional Blockade of Platelet-Derived Growth Factor Receptor-β But Not of Receptor-α Prevents Vascular Smooth Muscle Cell Accumulation in Fibrous Cap Lesions in Apolipoprotein E-Deficient Mice", Circulation, 103: 2955-2960, 2001

Sato et al. "Tie-1 and Tie-2 Define Another Class of Putative Receptor Tyrosine Kinases Genes Expressed in Early Embryonic Vascular System", Proc. Natl. Acad. Sci. USA, 90: 9355-9358, 1993.

Schlaeger et al. "Vascular Endothelial Cell Lineage-Specific Promoter in Transgenic Mice", Development, 121: 1089-1098, 1995.

Shimo et al. "Connective Tissue Growth Factor as a Major Angiogenic Agent That Is Induced by Hypoxia in A Human Breast Cancer Cell Line", Cancer Letters, 174: 57-64, 2001.

Soriano et al. "Targeted Disruption of the C-SRC Proto-Oncogene Leads to Osteopetrosis in Mice", Cell, 64: 693-702, 1991.

Stefanidakis et al. "Identification of a Negatively Charged Peptide Motif Within the Catalytic Domain of Progelatinases That Mediates Binding to Leukocyte β2 Integrins", The Journal of Biological Chemistry, 278(36): 34674-34684, 2003.

Strasser et al. "Apoptosis Signaling", Annual Review of Biochemistry, 69: 217-245, 2000.

Sun et al. "Functional Analysis of the Preproendothelin-1 Gene Promoter in Pulmonary Epithelial Cells and Monocytes", Biochemical and Biphysical Research Communications, 221(3): 647-652, 1996. p. 649 last §—p. 651, § 1.

Van de Stolpe et al. "Intercellular Adhesion Molecule-1", Journal of Molecular Medicine, 74(1): 13-33, 1996. Abstract.

Wang et al. "Molecular Cloning of the Complementary DNA for Human Tumor Necrosis Factor", Science, New Series, 228(4696): 149-154, 1985.

Watkins et al. "The 'Adenobody' Approach to Viral Targeting: Specific and Enhanced Adenoviral Gene Delivery", Gene Therapy, 4: 1004-1012, 1997.

West et al. "Endothelial Cell Proliferation and Diabetic Retinopathy", The Lancet, 1: 715-716, 1988.

Whitaker et al. "Induction of Functional Neovascularization by Wisker Stimulation After Focal Ischemia", Abstract Viewer and Itinery Planner, Society for Neuroscience, 2003: Abstract No. 789. 12, Nov. 2003. 33rd Annual Meeting of the Society of Neuroscience, New Orleans, LA, USA, Nov. 8-12, 2003.

Williams et al. "Hypoxia and Oxidative Stress in Breast Cancer Tumour Hypoxia—Therapeutic Considerations", Breast Cancer Research, 3: 328-331, 2001.

Wong et al. "Human GM-CSF: Molecular Cloning of the Complementary DNA and Purification of the Natural and Recombinant Proteins", Science, New Series, 228(4701): 810-815, 1985.

Wu et al. "Chimeric PSA Enhancers Exhibit Augmented Activity in Prostate Cancer Therapy Vectors", Gene Therapy, 8: 1416-1426, 2001.

Yanagisawa-Miwa et al. "Salvage of Infarcted Myocardium by Angiogenic Action of Basic Fibroblast Growth Factor", Science, New Series, 257(5075): 1401-1403, 1992.

International Search Report Dated Sep. 18, 2008 From the International Searching Authority Re.: Application No. PCT/IL07/00242.

Official Action Dated Oct. 2, 2008 From the US Patent Office Re.: U.S. Appl. No. 11/359,513.

Written Opinion dated Sep. 18, 2008 From the International Searching Authority Re.: Application No. PCT/IL07/00242.

Communication Pursuant to Article 96(2) EPC Dated Apr. 17, 2007 from the European Patent Office Re.: Application No. EP 02801473. 6.

1st Office Action dated Oct. 13, 2006 from the Patent Office of the People's Republic of China Re.: Application No. CN 03815262. 2—English Translation only.

Communication Pursuant to Article 96(2) EPC Dated Jul. 31, 2006 from the European Patent Office Re.: Application No. EP 03717516. 3.

International Preliminary Examination Report Dated Jan. 28, 2005 from the International Preliminary Examining Authority by the Patent Cooperation Treaty Re.: Application No. PCT/IL01/01059.

Written Opinion Dated Nov. 2, 2004 from the International Preliminary Examining Authority by the Patent Cooperation Treaty Re.: Application PCT/IL01/01059.

International Search Report Dated Dec. 2, 2002 from the International Searching Authority by the Patent Cooperation Treaty Re.: Application No. PCT/IL02/00339.
Official Action Dated Apr. 27, 2008 from the Korean Intellectual Property Office Re.: Application No. 2004-7005720 and its translation in English.
Written Opinion Dated Oct. 29, 2003 from the International Preliminary Examining Authority by the patent Cooperation Treaty Re.: Application No. PCT/IL02/00339.
International Search Report Dated Aug. 4, 2006 from the International Searching Authority by the Patent Cooperation Treaty Re.: Application No. PCT/IL05/01195.
Office Action Dated Jul. 14, 2004 from the US Patent and Trademark Office Re.: U.S. Appl. No. 10/135,447.
Supplementary Partial European Search Report Dated Nov. 15, 2004 from the European Patent Office Re.: Application EP 01996590.
International Search Report or the Declaration Dated May 4, 2004 from the International Searching Authority by the Patent Cooperation Treaty Re.: Application No. PCT/IL01/01059.
International Search Report or the Declaration Dated Jan. 28, 2005 from the International Searching Authority by the Patent Cooperation Treaty.
First Examination Report Dated Apr. 13, 2006 from the Government of India Patent Office. Re.: Application No. 743/CHENP/2003—in English only.
Examination Report Dated Aug. 3, 2006 from the Intellectual Property Office of New Zealand Re.: Application No. 536578.
Supplementary European Search Report Dated Mar. 21, 2006 from the European Patent Office Re.: Application No. EP 02801473.6.
Official Communication Dated Feb. 28, 2008 from the Instituto Mexicano de la Propiedad Industrial Re.: Application No. PA/a/2003/004325, and its Summary in English by Associate.
Written Opinion of the International Searching Authority Dated Aug. 4, 2006 from the International Searching Authority by the Patent Cooperation Treaty Re.: Application No. PCT/IL05/01195.
Office Communication Dated Apr. 6, 2007 from the US Patent and Trademark Office Re.: U.S. Appl. No. 10/975,619.
Communication Pursuant to Article 94(3) EPC Dated May 29, 2008 from the European Patent Office Re.: Application No. 05806361.1.
Communication pursuant to Article 96(2) EPC Dated Apr. 17, 2007 from the European Patent Office Re.: Application No. EP 02801473.6.
Second Official Action Dated May 28, 2008 from the Japanese Patent Office Re.: Application No. 202-543626.
Examination Report Dated Sep. 5, 2005 from the Intellectual Property Office of New Zealand Re.: Application 536578.
International Preliminary Examination Report Dated May 26, 2005 from the International Preliminary Examining Authority by the Patent Cooperation Treaty Re.: Application PCT/IL03/00347.
International Preliminary Examination Report Dated Jan. 5, 2005 from the International Preliminary Examining Authority by the Patent Cooperation Treaty Re.: Application No. PCT/IL02/00339.
Official Communication Dated Feb. 1, 2008 from the Instituto Mexicano de la Propiedad Industrial Re.: Application No. PA/a/2004/003514 and its summary in English by Associate.
Office Communication Dated Apr. 10, 2008 from the US Patent and Trademark Office Re.: U.S. Appl. No. 10/975,619.
Communication Pursuant to Article 96(2) EPC Dated May 3, 2006. from the European Patent Office Re.: Application No. EP 01996590.4.
Official Action Dated Oct. 2, 2008 From the US Patent and Trademark Office Re.: U.S. Appl. No. 11/359,513.
Communication Pursuant to Article 96(2) EPC Dated Apr. 27, 2007 from the European Patent Office Re.: Application No. EP 01996590.4.
Official Action Dated Jul. 31, 2007 from the Japanese Patent Office Re.: Application No. 2004-501545.
First Official Action Dated Jul. 31, 2007 from the Japanese Patent Office Re.: Application No. 2002-543626.
Official Communication Dated Jul. 18, 2007 from the Instituto Mexicano de la Propiedad Industrial Re.: Application No. PA/a/2004/010711 and its English summary by Associate.
Supplementary European Search Report Dated Oct. 14, 2005 from the European Patent Office Re.: Application No. EP 03717516.
Communication with Supplementary Search Report Dated Oct. 17, 2007 from The European Patent Office Re.: Application No. EP 05806361-1.
Supplementary European Search Report Dated Oct. 17, 2007 from the European Patent Office Re.: Application EP 05806361.
Official Action Dated Oct. 16, 2007 from the Japanese Patent Office Re.: Application No. 2003-536253.
Communication Pursuant to Article 94(3) EPC Dated Feb. 10, 2007 From the European Patent Office Re.: Application No. 02801473.6.
Communication Pursuant to Article 94(3) EPC Dated Feb. 16, 2009 From the European Patent Office Re.: Application No. 05806361.1.
Communication Pursuant to Article 94(3) EPC Dated Apr. 27, 2007 From the European Patent Office Re.: Application No. 01996590.4.
Communication Pursuant to Article 96(2) EPC Dated Dec. 21, 2006 From the European Patent Office Re.: Application No. 01996590.4.
Examination Report Dated Apr. 3, 2009 From the Intellectual Property Office of New Zealand Re.: Application No. 555612.
International Preliminary Examination Report Dated Jan. 5, 2005 From the International Preliminary Examining Authority Re.: Application No. PCT/IL02/00339.
International Preliminary Report on Patentability Dated Jan. 22, 2009 From the International Bureau of WIPO Re.: Application No. PCT/IL2007/000242.
International Preliminary Report on Patentability Dated May 24, 2007 From the International Bureau of WIPO Re.: Application No. PCT/IL2005/001195.
International Search Report Dated Apr. 29, 2009 From the International Searching Authority Re.: Application No. PCT/IL08/00543.
Invitation to Pay Additional Fees Dated Jun. 1, 2006 From the International Searching Authority Re.: Application No. PCT/IL05/01195.
Notice of Allowance Dated Aug. 14, 2008 From the US Patent and Trademark Office Re.: U.S. Appl. No. 10/075,619.
Office Action Dated Jan. 10, 2008 From the Israeli Patent Office Re.: Application No. 155940.
Office Action Dated Sep. 20, 2007, From the Israeli Patent Office Re.: Application No. 155940.
Official Action Dated Jan. 4, 2008 From the US Patent and Trademark Office Re.: U.S. Appl. No. 10/988,487.
Official Action Dated Jun. 4, 2007 From the US Patent and Trademark Office Re.: U.S. Appl. No. 10/975,619.
Official Action Dated May 6, 2009 From the US Patent and Trademark Office Re.: U.S. Appl. No. 11/359,513.
Supplementary European Search Report Dated Mar. 21, 2006 From the European Patent Office Re.: Application No. 02801473.6.
Translation of Notice of the Reason for Rejection Dated Jan. 7, 2009 From the Korean Intellectual Property Office Re.: Application No. 2008-7018598.
Written Opinion Dated Apr. 29, 2009 From the International Searching Authority Re.: Application No. PCT/IL08/00543.

* cited by examiner

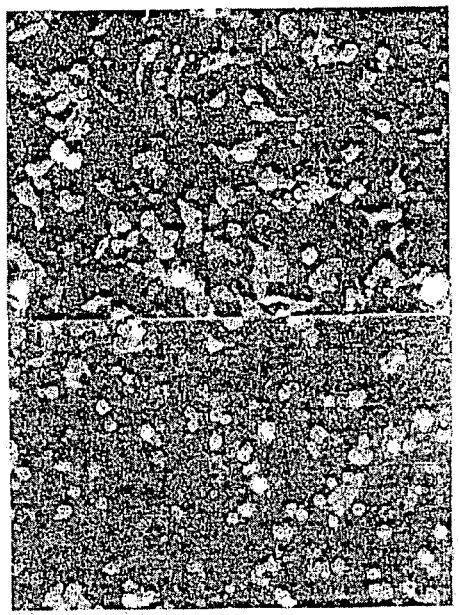
Fig. 2a  Fig. 2b
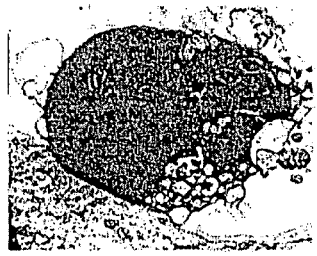
Fig. 3a
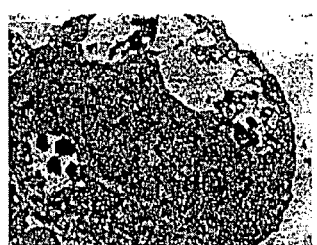
Fig. 3b
Fig. 3c
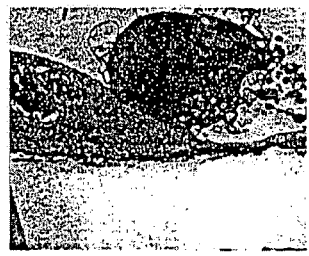
Fig. 3d
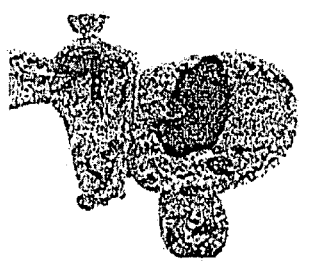
Fig. 3e
Fig. 3f

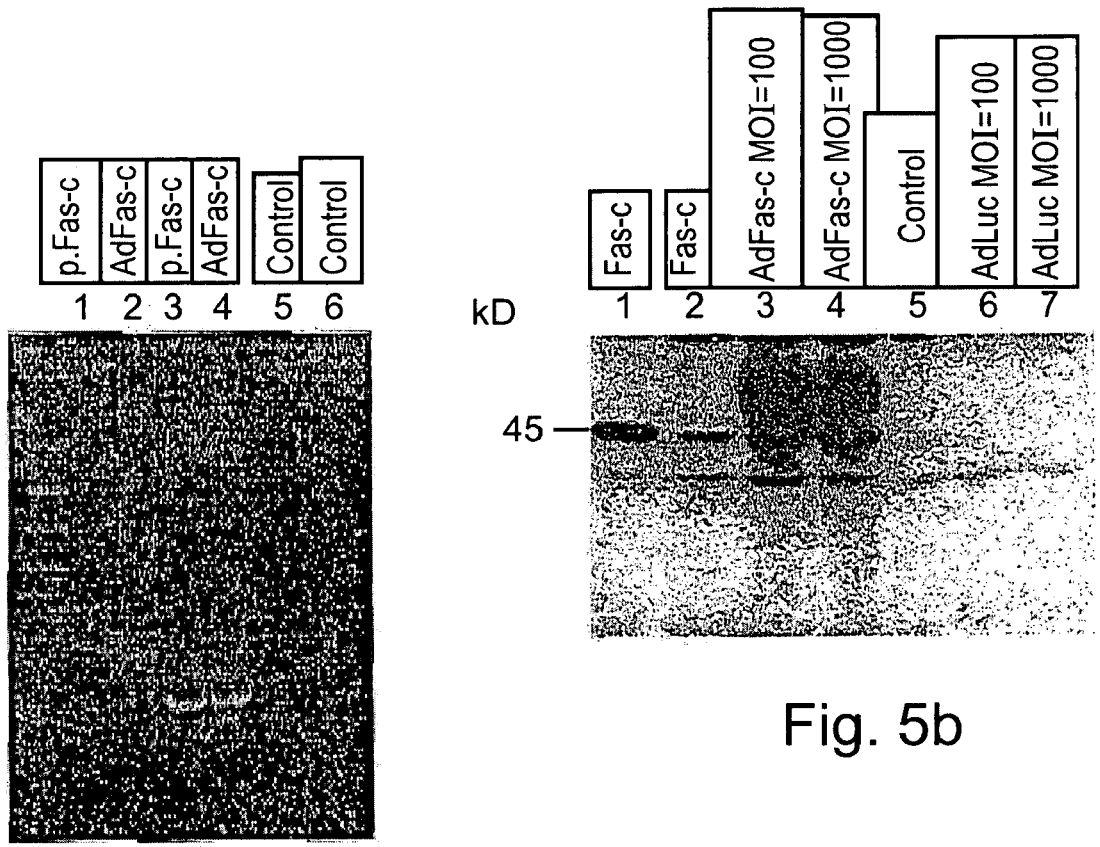
Fig. 5a
Fig. 5b
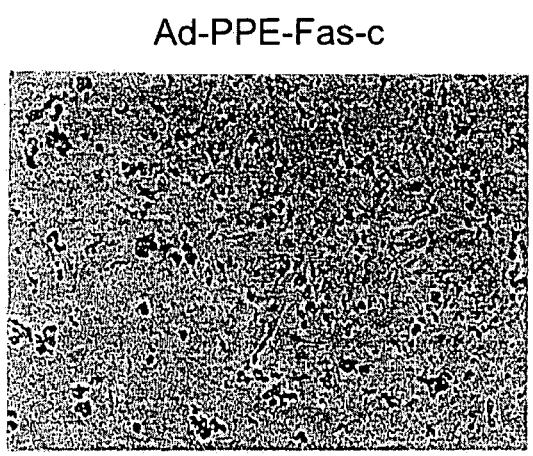
Fig. 6a
Ad-PPE-Fas-c
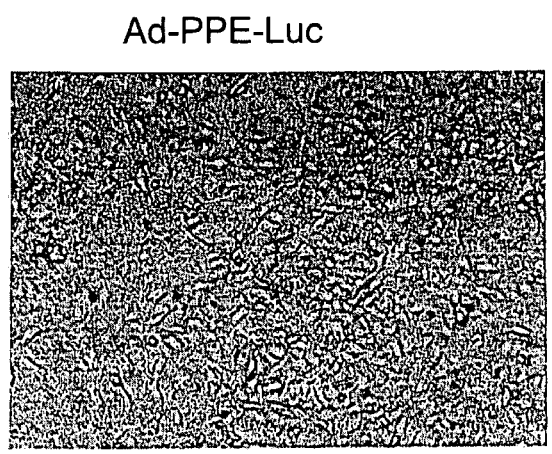
Fig. 6b
Ad-PPE-Luc Ad-PPE-Fas-c Ad-PPE-Luc 2.7 cm x 1.8 cm
Control-saline 1.4 cm x 1.2 cm
Ad-PPE1-3x-Fas-c

POLYNUCLEOTIDE CONSTRUCTS, PHARMACEUTICAL COMPOSITIONS AND METHODS FOR TARGETED DOWNREGULATION OF ANGIOGENESIS AND ANTICANCER THERAPY This application is a National Phase application of PCT Application No. PCT/IL02/00339, filed May 1, 2002, which claims the benefit of U.S. Provisional Patent Application No. 60/330,118, filed Oct. 19, 2001.

FIELD AND BACKGROUND OF THE INVENTION

The present invention relates to a nucleic acid constructs, pharmaceutical compositions and methods which can be used to downregulate angiogenesis in specific tissue regions of a subject. More particularly, the present invention relates to nucleic acid constructs, which can be used to activate apoptosis in specific cell subsets, thus, enabling treatment of diseases characterized by excessive or aberrant neovascularization or cell growth.

Angiogenesis is the growth of new blood vessels, a process that depends mainly on locomotion, proliferation, and tube formation by capillary endothelial cells. During angiogenesis, endothelial cells emerge from their quiescent state and proliferate rapidly. Although the molecular mechanisms responsible for transition of a cell to angiogenic phenotype are not known, the sequence of events leading to the formation of new vessels has been well documented [Hanahan, D., Science 277, 48-50, (1997)]. The vascular growth entails either endothelial sprouting [Risau, W., Nature 386, 671-674, (1997)] or intussusceptions [Patan, S., et al; Microvasc. Res. 51, 260-272, (1996)]. In the first pathway, the following sequence of events may occur: (a) dissolution of the basement of the vessel, usually a post capillary venule, and the interstitial matrix; (b) migration of endothelial cells toward the stimulus; (c) proliferation of endothelial cells trailing behind the leading endothelial cell (s); (d) formation of lumen (canalization) in the endothelial array/sprout; (e) formation of branches and loops by confluencial anastomoses of sprouts to permit blood flow; (f) investment of the vessel with pericytes (i.e., periendothelial cells and smooth muscle cells); and (g) formation of basement membrane around the immature vessel. New vessels can also be formed via the second pathway: insertion of interstitial tissue columns into the lumen of pre-existing vessels. The subsequent growth of these columns and their stabilization result in partitioning of the vessel lumen and remodeling of the local vascular network.

A variety of angiogenic factors govern the angiogenic process. It is understood that during pathology, the fine balance between pro-angiogenic factors and anti-angiogenic factors is disrupted, thereby eliciting nonself-limiting endothelial and periendothelial cell-proliferation. Until recently, the angiogenesis that occurs in diseases of ocular neovascularization, arthritis, skin diseases, and tumors, had been difficult to suppress therapeutically.

Therefore, the fundamental goal of all anti-angiogenic therapy is to return foci of proliferating microvessels to their normal resting state, and to prevent their regrowth [Cancer: Principles & Practice of Oncology, Fifth Edition, edited by Vincent T. DeVita, Jr., Samuel Hellman, Steven A. Rosenberg. Lippincott-Raven Publishers, Philadelphia. (1997)].

Anti-angiogenic therapy is a robust clinical approach, as it can delay the progression of tumor growth (e.g., retinopathies, benign and malignant angiogenic tumors).

In general, every disease caused by uncontrolled growth of capillary blood vessels such as diabetic retinopathy, psoriasis, arthritis, hemangiomas, tumor growth and metastasis is a target for anti-angiogenic therapy.

For example, the progressive growth of solid tumors beyond clinically occult sizes (e.g., a few $mm^3$) requires the continuous formation of new blood vessels, a process known as tumor angiogenesis. Tumor growth and metastasis are angiogenesis-dependent. A tumor must continuously stimulate the growth of new capillary blood vessels to deliver nutrients and oxygen for the tumor itself to grow. Therefore, either prevention of tumor angiogenesis or selective destruction of tumor's existing blood vessels (vascular targeting therapy) underlies anti-angiogenic tumor therapy.

Recently, a plethora of anti-angiogenic agents has been developed for the treatment of malignant diseases, some of which are already under clinical trials (for review see Herbst et al. (2002) Semin. Oncol. 29:66-77).

The most studied target for tumor anti-angiogenic treatment is the dominant process regulating angiogenesis in human i.e., the interaction of vascular endothelial growth factor (VEGF) with its receptor (VEGFR). Agents which regulate VEGFR pro-angiogenic action include (i) antibodies directed at the VEGF protein itself or to the receptor (e.g., rhuMAb VEGF); (ii) small molecule compounds directed to the VEGFR tyrosine kinase (e.g., ZD6474 and SU5416); (iii) VEGFR targeted ribozymes.

Other novel angiogenesis inhibitors include 2-Methoxyestradiol (2-ME2) a natural metabolite of estradiol that possesses unique anti-tumor and anti-angiogenic properties and angiostatin and endostatin—proteolytic cleavage fragments of plasminogen and collagen XVIII, respectively.

Though promising in pre-clinical models, to date systemic administration of all anti-angiogenic agents tested in clinical trials, have shown limited rate of success and considerable toxicities including thrombocytopenia, leukopenia and hemoptysis. These results suggest that there may be limits to the use of current tumor anti-angiogenic agents as therapy for advanced malignancies. O'Reilly et al. have shown that the latency between the initiation of anti-angiogenic therapy and antitumor effect may result in initial tumor progression before response to therapy [O'Reilly S et al. (1998) Proc Am Soc Clin Oncol 17:217a]. Furthermore, recent studies suggest that the regulation of angiogenesis may differ among capillary beds, suggesting that anti-angiogenic therapy may need to be optimized on an organ/tissue-specific basis [Arap et al. (1998) Science 279:377-380].

Interestingly, poor results have also been obtained when anti-angiogenic therapy (e.g., heparin, heparin-peptide treatment) directed at smooth muscle cell proliferation has been practiced on myocardial ischemia in patients with coronary artery disease [Liu et al., Circulation, 79:1374-1387 (1989); Goldman et al., Atherosclerosis, 65:215-225 (1987); Wolinsky et al., JACC, 15 (2):475-481 (1990)]. Various limitations associated with the use of such agents for the treatment of cardiovascular diseases included: (i) systemic toxicity creating intolerable level of risk for patients with cardiovascular diseases; (ii) interference with vascular wound healing following surgery; (iii) possible damage to surrounding endothelium and/or other medial smooth muscle cells.

In-light of these and the inherent obstacles associated with systemic administration of anti-angiogenic factors (i.e., manufacturing limitations based on in-vitro instability and high doses required; and peak kinetics of bolus administration attributing to sub-optimal effects) limit the effective use of angiogenic factors in treating neo-vascularization associated diseases.

With the identification of new genes that regulate the angiogenic process, somatic gene therapy has been attempted to overcome these limitations. Although, great efforts have been directed towards developing methods for gene therapy of cancer, cardiovascular and peripheral vascular diseases, there is still major obstacles to effective and specific gene delivery [for review see, Feldman A L. (2000) Cancer 89(6): 1181-94] In general, the main limiting factor of gene therapy with a gene of interest, using a recombinant viral vector as a shuttle is the ability to specifically direct the gene of interest to the target tissue.

Attempts to overcome these limitations included the use of tissue-specific promoters conjugated to cytotoxic genes. For example, endothelial cell targeting of a cytotoxic gene, expressed under the control endothelial-specific promoters has been described by Jagger et al who used the KDR or E-selectin promoter to express TNFα specifically in endothelial cells [Jaggar R T. Et al. Hum Gene Ther (1997) 8(18): 2239-47]. Ozaki et al used the von-Willebrand factor (vWF) promoter to deliver herpes simplex virus thymidine kinase (HSV-tk) to HUVEC [Hum Gene Ther (1996) 7(13):1483-90]. However, these promoters showed only weak activity and did not allow for high levels of expression.

An alternate approach presented by Kong and Crystal included a tumor specific expression of anti-angiogenic factors. To date, however, the toxicity of recombinant forms of endogenous anti-angiogenic agents has not been demonstrated although some synthetic anti-angiogenic agents have been associated with toxicity in preclinical models [Kong and Crystal (1998) J. Natl. Cancer Inst. 90:273-76].

Angiostatin has also been used as a possible anti-angiogenic agent (Falkman et al, Cell 1997 Jan. 24;88(2):277-85), however due to the redundancy of factors involved in regulation of angiogenesis in tumors, it is highly unlikely that angiostatin therapy alone would be effective.

There is thus a widely recognized need for, and it would be highly advantageous to have a novel approach for efficiently down-regulating angiogenesis in specific tissue regions of a subject while being devoid of the toxic side effects characterizing prior art anti-angiogenesis approaches.

SUMMARY OF THE INVENTION

According to one aspect of the present invention there is provided a nucleic acid construct comprising: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in a specific tissue or cell; wherein the ligand binding domain is selected such that it is capable of binding a ligand present in the specific tissue or cell, whereas binding of the ligand to the ligand binding domain activates the effector domain of the apoptosis signaling molecule.

According to further features in preferred embodiments of the invention described below, there is provided a mammalian cell transformed with the nucleic acid construct described above.

According to another aspect of the present invention there is provided a method of down-regulating angiogenesis in a tissue of a subject, the method comprising administering to the subject a nucleic acid construct designed and configured for generating apoptosis in a sub-population of angiogenic cells, the nucleic acid construct including: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in the sub-population of angiogenic cells; wherein the ligand binding domain is selected such that it is capable of binding a ligand present in, or provided to, the sub-population of angiogenic cells, whereas binding of the ligand to the ligand binding domain activates the effector domain of the apoptosis signaling molecule, thereby down-regulating angiogenesis in the tissue.

According to further features in preferred embodiments of the invention described below, the method further comprising administering the ligand to the subject in a manner suitable for providing the ligand to the sub-population of angiogenic cells.

According to yet another aspect of the present invention there is provided method of down-regulating angiogenesis in a tissue of a subject, the method comprising: (a) administering to the subject a nucleic acid construct designed and configured for generating apoptosis in a sub-population of angiogenic cells, the nucleic acid construct including: (i) a first polynucleotide region encoding a chimeric polypeptide including a ligand binding domain fused to an effector domain of an apoptosis signaling molecule, wherein the effector domain is selected such that it is activated following binding of a ligand to the ligand binding domain; and (ii) a second polynucleotide region encoding a cis acting regulatory element being for directing expression of the chimeric polypeptide in the sub-population of angiogenic cells; and (b) administering to the subject the ligand, thereby down-regulating angiogenesis in the tissue.

According to still further features in the described preferred embodiments the administering the ligand to the subject is effected by a method selected from the group consisting of: (i) systemic in-vivo administration; (ii) ex-vivo administration to cells removed from a body of the subject, the cells subsequently reintroduced into the body of the subject; and (iii) local in-vivo administration.

According to still further features in the described preferred embodiments the cis-acting regulatory element is an endothelial cell-specific or periendothelial cell-specific promoter selected from the group consisting of the PPE-1 promoter, the PPE-1-3x promoter, the TIE-1 promoter, the TIE-2 promoter, the Endoglin promoter, the von Willerband promoter, the KDR/flk-1 promoter, The FLT-1 promoter, the Egr-1 promoter, the ICAM-1 promoter, the VCAM-1 promoter, the PECAM-1 promoter, the CArG box element and aortic carboxypeptidase-like protein (ACLP) promoter.

According to still further features in the described preferred embodiments the ligand binding domain is a ligand-binding domain of a cell-surface receptor.

According to still further features in the described preferred embodiments the cell-surface receptor is selected from the group consisting of a receptor tyrosine kinase, a receptor serine kinase, a receptor threonine kinase, a cell adhesion molecule and a phosphatase receptor.

According to still further features in the described preferred embodiments the apoptosis signaling molecule is selected from the group consisting of Fas and TNFR.

According to still another aspect of the present invention there is provided a pharmaceutical composition for down regulating angiogenesis in a tissue of a subject, the pharmaceutical composition comprising as an active ingredient a nucleic acid construct designed and configured for generating apoptosis in a subpopulation of angiogenic cells and a pharmaceutical acceptable carrier, the nucleic acid construct including: (a) a first polynucleotide region encoding a chimeric polypeptide including a ligand binding domain fused to an effector domain of an apoptosis signaling molecule; and (b) a second polynucleotide region encoding a cis acting regulatory element being for directing expression of the chimeric polypeptide in the subpopulation of angiogenic cells; wherein the ligand binding domain is selected such that it is capable of binding a ligand present in the specific tissue or cell, whereas binding of the ligand to the ligand binding domain activates the effector domain of the apoptosis signaling molecule.

According to an additional aspect of the present invention there is provided a method of treating a disease or condition associated with excessive neo-vascularization, the method comprising administering a therapeutically effective amount of a nucleic acid construct designed and configured for generating apoptosis in a sub-population of angiogenic cells, the nucleic acid construct including: (i) a first polynucleotide region encoding a chimeric polypeptide including a ligand binding domain fused to an effector domain of an apoptosis signaling molecule; and (ii) a second polynucleotide region encoding a cis acting regulatory element being for directing expression of the chimeric polypeptide in the sub-population of angiogenic cells; wherein the ligand binding domain is selected such that it is capable of binding a ligand present in, or provided to, the sub-population of angiogenic cells, whereas binding of the ligand to the ligand binding domain activates the effector domain of the apoptosis signaling molecule, thereby down-regulating angiogenesis in the tissue and treating the disease or condition associated with excessive neo-vascularization.

According to yet an additional aspect of the present invention there is provided a method of treating a tumor in a subject, the method comprising administering a therapeutically effective amount of a nucleic acid construct designed and configured for generating apoptosis in cells of the tumor, the nucleic acid construct including: (i) a first polynucleotide region encoding a chimeric polypeptide including a ligand binding domain fused to an effector domain of an apoptosis signaling molecule; and (ii) a second polynucleotide region encoding a cis acting regulatory element being for directing expression of the chimeric polypeptide in the cells of the tumor; wherein the ligand binding domain is selected such that it is capable of binding a ligand present in, or provided to, the cells of the tumor, whereas binding of the ligand to the ligand binding domain activates the effector domain of the apoptosis signaling molecule to thereby direct apoptosis in the cells of the tumor.

According to still further features in the described preferred embodiments the method further comprising administering the ligand to the subject in a manner suitable for providing the ligand to the cells of the tumor.

According to still further features in the described preferred embodiments the cis acting regulatory element is selected from the group consisting of the gastrin-releasing peptide (GRP) promoter, the hTERT promoter, the Hexokinase type II promoter and the L-plastin promoter.

The present invention successfully addresses the shortcomings of the presently known configurations by providing a novel approach for efficiently downregulating angiogenesis and tumor cell proliferation in a specific and targeted manner.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2a-b illustrate apoptotic activity of the pro-apoptotic genes, Fas chimera and TNFR1. FIG. 2a—illustrates Bovine Aortic Endothelial Cells (BAEC) transfected with either pcDNA-3-TNFR1 (lower panel) or control empty vector (upper panel) and an expression plasmid encoding GFP. FIG. 2b—illustrates 293 Cells transfected with either pcDNA-3-Fas-c (lower panel) or control empty vector (upper panel) and an expression plasmid encoding GFP. Transfected cells were visualized using fluorescence microscopy and apoptotic activity was morphologically determined.

FIGS. 3a-f are electron microscopy images of BAEC cells transfected with pro-apoptotic genes. 24 hours post transfection, BAEC cells were fixed in 2.5% glutaraldehyde and processed. Presented are cells in successive stages of the apoptotic process.

FIG. 5a represents a PCR analysis of AdPPE-Fas-c. Lanes 1-2—PCR products obtained using primers encompassing the PPE-1 promoter and Fas-c gene. Lanes 3-4—PCR products obtained using Fas-c primers. Lanes 5-6—PCR products obtained in the absence of template DNA.

FIG. 5b is a western blot analysis of AdPPE-Fas-c transfected BAEC cells. Protein samples were resolved by SDS-PAGE, transferred to nitrocellulose membrane and probed with a polyclonal antibody directed against the extracellular portion of TNFR1. Lane 1-2—pcDNA3-Fas-c BAEC transfected cells (positive control). Lane 3-4—BAEC cells transfected with the indicated MOI of AdPPE-Fas-c viruses. Lane 5—non-transfected cells. Lane 6-7—BAEC cells transfected with the indicated MOI of AdPPE-Luc.

FIGS. 6a-d are photomicrographs illustrating the effect of Fas-chimera over-expression on apoptosis of endothelial cells. BAEC cells were infected with: Ad-PPE-1-3x-Fas-chimera (FIG. 6a); Ad-PPE-1-3x-luciferase (FIG. 6b); Ad-PPE-1-3x-Fas-chimera and Ad-PPE1-3x-GFP (FIG. 6c); Ad-PPE-1-3x-luciferase and Ad-PPE-1-3x-GFP; each at MOI 1000 (FIG. 6d). Photomicrographs were taken 72 h post infection at ×10 magnification.

FIG. 10b—NSF infected with a control virus. FIG. 10c—NSF infected with Ad-CMV-Fas-chimera. FIG. 10d—NSF infected with Ad-CMV-Fas-chimera and incubated with TNF (10 ng/ml).

FIG. 11a—tumor areas, measured during treatment period. FIG. 11b—tumor weights at end of treatment period. FIG. 11c—an image representing the state of the tumor in the Ad-PPE-1-3x-Fas-c treated mouse and the control mouse.

DESCRIPTION OF THE PREFERRED EMBODIMENTS

Figure 1A:
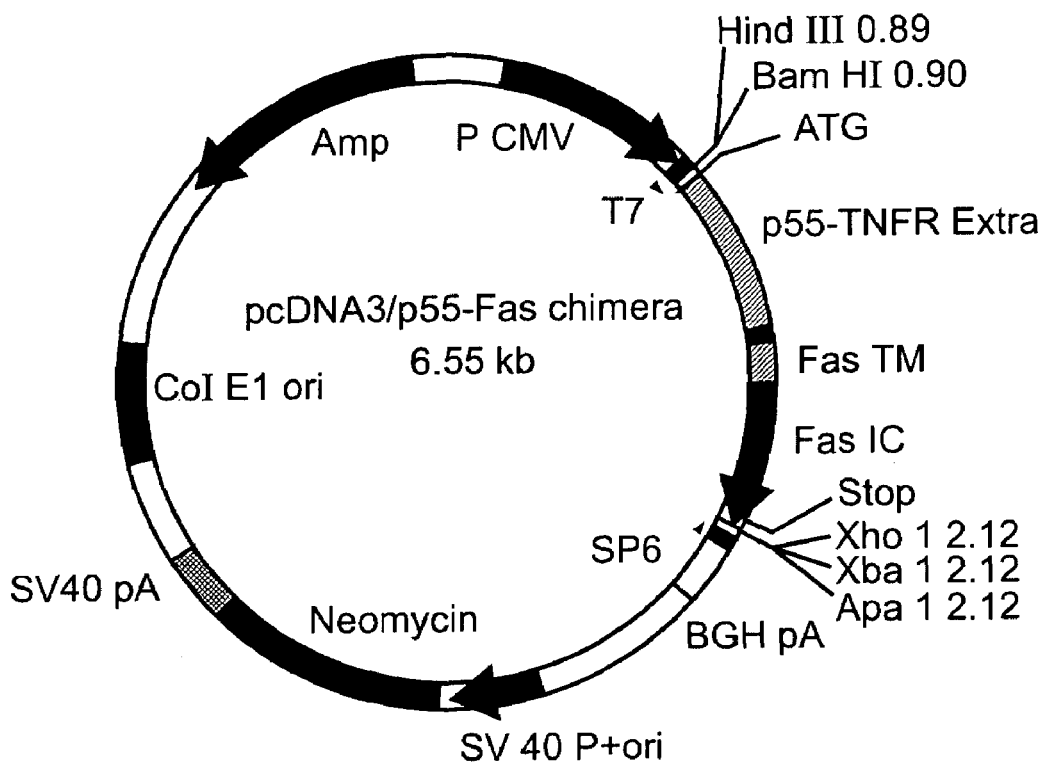
FIGS. 1a-b are schematic illustrations of Fas chimera gene constructed from the extracellular region of TNFR1 and the trans-membrane and intracellular regions of Fas and cloned into pcDNA3 plasmid (a) or into adenoviral vectors (b).

The present invention is of nucleic acid constructs and methods, which can be used to treat diseases characterized by excessive or aberrant neovascularization or cell growth. Specifically, the present invention can be used to specifically target and kill cells involved in angiogenesis, thus enabling down-regulation of angiogenesis and anti-tumor therapy.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

One of the most fundamental goals of anti-angiogenic therapy is to return foci of proliferating microvessels to their normal resting state, and to prevent their re-growth.

To date, anti-angiogenic therapy approaches, which employ systemic administration of anti-angiogenic agents have been employed with limited success mostly due to the toxic side effects which lead to the formation of thrombocytopenia, leukopenia and/or hemoptysis in the treated individual. The toxic side effects associated with prior art approaches is a result of non-specific expression of the anti-angiogenic agents employed and exposure of healthy tissue to these agents or the redundancy and thus non-effectiveness of the anti-angiogenic agents used.

While reducing the present invention to practice, the present inventors have uncovered that a combination of tissue-specific expression and specific activation of a pro-apoptotic agent enables selective apoptosis of cells involved in angiogenesis without exposing non-targeted tissue or cells to these agents, thus, avoiding the toxic side effects and redundancy characterizing prior art treatment approaches.

Thus, according to one aspect of the present invention there is provided a method of down-regulating angiogenesis in a tissue of a subject. As used herein, the phrase "down-regulating angiogenesis" refers to either slowing down or stopping the angiogenic process, which lead to formation of new blood vessels.

The method according to this aspect of the present invention is effected by administering to the subject a nucleic acid construct designed and configured for generating apoptosis in a sub-population of angiogenic cells. As used herein, the phrase "angiogenic cells" refers to any cells, which participate or contribute to the process of angiogenesis. Thus, angiogenic cells include but are not limited to, endothelial cells, smooth muscle cells.

In order to direct specific expression of an apoptotic agent in a subpopulation of angiogenic cells, the nucleic acid construct of the present invention includes a first polynucleotide region encoding a chimeric polypeptide including a ligand binding domain which can be, for example, a cell-surface receptor domain of a receptor tyrosine kinase, a receptor serine kinase, a receptor threonine kinase, a cell adhesion molecule or a phosphatase receptor fused to an effector domain of an apoptosis signaling molecule such as, for example, Fas, TNFR, and TRAIL.

Such a chimeric polypeptide can include any ligand binding domain fused to any apoptosis signaling domain as long as activation of the ligand binding domain, i.e., via ligand binding, triggers apoptosis signaling via the effector domain of the apoptosis signaling molecule.

Selection of the ligand binding domain and the apoptosis signaling domain fused thereto is affected according to the type of angiogenic cell targeted for apoptosis. For example, when targeting specific subset of endothelial cells (e.g., proliferating endothelial cells, or endothelial cells exhibiting a tumorous phenotype), the chimeric polypeptide includes a ligand binding domain capable of binding a ligand naturally present in the environment of such endothelial cells and preferably not present in endothelial cells of other non-targeted tissues (e.g., TNF, VEGF ). Such a ligand can be secreted by endothelial cells (autocrine), secreted by neighboring tumor cells (paracrine) or specifically targeted to these endothelial cells.

Examples of suitable chimeric polypeptides are provided in Examples 2 of the Examples section which follows. Preferably, the chimeric polypeptide is the Fas-c chimera which is described in detail in Examples 2-4 of the Examples section which follows.

The use of such a chimeric polypeptide is particularly advantageous, since, as shown in the Examples section herein under, it enables efficient and robust activation of apoptosis in a specific subset of angiogenic cells while avoiding activation in other subset of cells, which are not targeted for apoptosis.

To further enhance cell specificity of apoptosis, the nucleic acid construct of the present invention further includes a second polynucleotide region, which encodes a cis acting regulatory element (e.g., promoter and/or enhancer) capable of directing expression of the chimeric polypeptide in the sub-population of angiogenic cells.

Examples of suitable promoters/enhancers which can be utilized by the nucleic acid construct of the present invention include the endothelial-specific promoters: preproendothelin-1, PPE-1 promoter (Harats D, J Clin Invest. 1995 March; 95(3):1335-44)., the PPE-1-3x promoter [PCT/IL01/01059; Varda-Bloom N, Gene Ther 2001 June;8(11):819-27], the TIE-1 (S79347, S79346) and the TIE-2 (U53603) promoters [Sato T N, Proc Natl Acad Sci USA 1993 Oct. 15;90(20): 9355-8], the Endoglin promoter [Y11653; Rius C, Blood 1998 Dec. 15;92(12):4677-90], the von Willerbrand factor [AF152417; Collins C J Proc Natl Acad Sci USA 1987 July ; 84(13):4393-7], the KDR/flk-1 promoter [X89777, X89776; Ronicke V, Circ Res 1996 August ;9(2):277-85],The FLT-1 promoter [D64016 AJ224863; Morishita K,: J Biol Chem 1995 Nov. 17;270(46):27948-53], the Egr-1 promoter [AJ245926; Sukhatme V P, Oncogene Res 1987 September-October;1(4):343-55], the E-selectin promoter [Y12462; Collins T J Biol Chem 1991 Feb. 5;266(4):2466-73], The endothelial adhesion molecules promoters: ICAM-1 [X84737; Horley K J EMBO J 198]October;8(10):2889-96], VCAM-1 [M92431; Iademarco M F, J Biol Chem 1992 Aug. 15;267(23):16323-9], PECAM-1 [AJ313330 X96849; CD31, Newman P J, Science 1990 Mar. 9;247(4947):1219-22], the vascular smooth-muscle-specific elements: CArG box X53154 and aortic carboxypeptidase-like protein (ACLP) promoter [AF332596;Layne M D, *Circ Res.* 2002; 90: 728-736] and Aortic Preferentially Expressed Gene-1 [Yen-Hsu Chen J. Biol. Chem., Vol. 276, Issue 50, 47658-47663, Dec. 14, 2001].

Preferably, the promoter utilized by the construct of the present invention is functional in proliferating angiogenic cells, or angiogenic cells of a particular phenotype (e.g., tumorous). A promoter highly suitable for use with the present invention is the PPE-1-3x promoter which is further described in the Examples section which follows. A vector construct most suitable for use with the present invention is the widely used adenoviral vector and its derivatives.

The nucleic acid construct of the present invention can further include additional polynucleotide sequences such as for example, sequences encoding selection markers or reporter polypeptides, sequences encoding origin of replication in bacteria, sequences that allow for translation of several proteins from a single mRNA (IRES), sequences for genomic integration of the promoter-chimeric polypeptide encoding region and/or sequences generally included in mammalian expression vector such as pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

Preferably, the nucleic acid construct of the present invention is administered to the subject via, for example, systemic administration routes or via oral, rectal, transmucosal (especially transnasal), intestinal or parenteral administration routes. Systemic administration includes intramuscular, subcutaneous and intramedullary injections as well as intrathecal, direct intraventricular, intravenous, inrtaperitoneal, intranasal, intraocular injections or intra-tumoral.

Preferably, the subject is a mammal, more preferably, a human being, most preferably, a human being suffering from diseases characterized by excessive or abnormal neovascularization such as that characterizing tumor growth, proliferating diabetic retinopathy, arthritis and the like.

The nucleic acid constructs of the present invention can be administered to the subject per se or as part (active ingredient) of a pharmaceutical composition.

The prior art teaches of a number of delivery strategies which can be used to efficiently deliver naked or carrier provided polynucleotides into a wide variety of cell types (see, for example, Luft (1998) J Mol Med 76(2): 75-6; Kronenwett et al. (1998) Blood 91(3): 852-62; Rajur et al. (1997) Bioconjug Chem 8(6): 935-40; Lavigne et al. (1997) Biochem Biophys Res Commun 237(3): 566-71 and Aoki et al. (1997) Biochem Biophys Res Commun 231(3): 540-5).

As used herein a "pharmaceutical composition" refers to a preparation of one or more of the active ingredients or agents described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered nucleic acid construct. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient. In the context of the present invention, administration directly into tumor tissue is a relevant example of local administration.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredient of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. antisense oligonucleotide) effective to prevent, alleviate or ameliorate symptoms of a disorder (e.g., progressive loss of bone mass) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in an animal model, such as the murine Src deficient model of osteopetrosis (Boyce et al. (1992) J. Clin. Invest. 90, 1622-1627; Lowe et al. (1993) Proc. Natl. Acad. Sci. USA 90, 4485-4489; Soriano et al. (1991) Cell 64, 693-702), to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to levels of the active ingredient are sufficient to retard tumor progression (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The pharmaceutical compositions of the present invention may further include any additional ingredients which may improve the uptake of the nucleic acid construct by the cells, expression of the chimeric polypeptide encoded by the nucleic acid construct in the cells, or the activity of the expressed chimeric polypeptide.

For example, the uptake of adenoviral vectors into EC cells can be enhanced by treating the vectors with engineered antibodies or small peptides. Such "adenobody" treatment, was shown effective in directing adenovirus constructs to EGF receptors on cells (Watkins et al 1997, Gene Therapy 4:1004-1012). In addition, Nicklin et al have shown that A small peptide, isolated via phage display, increased specificity and efficiency of vectors in endothelial cells and decreased the expression in liver cells in culture (Nicklin et al 2000, Circulation 102:231-237). In a recent study, an FGF retargeted adenoviral vector reduced the toxicity of tk in mice (Printz et al 2000, Human Gene Therapy 11:191-204).

It will be appreciated that although targeting of cells exposed to the ligand is preferred, the present invention also envisages expression of the nucleic acid construct of the present invention in cells which are not exposed to, or naturally affected by the ligand. In such cases, the method of the present invention includes the step of administering such a ligand to the cells transformed. Such administration can be effected by using any of the above described administration methods. Preferably, the ligand is administered in a cell targeted manner, using for example antibody conjugated targeting, such that activation of apoptosis signaling is highly specific. This approach of apoptosis activation is described in more detail in the Examples section which follows.

Thus, the present invention provides nucleic acid constructs, pharmaceutical compositions including such constructs and methods of utilizing such constructs for downregulating angiogenesis in tissue regions characterized by excessive or abnormal angiogenesis.

Since the present invention enables targeted expression in specific cell subsets, it can also be modified and used in for treating various tumors.

Thus, according to another aspect of the present invention there is provided a method of treating tumors.

The method according to this aspect of the present invention is effected by expressing in tumor cells the chimeric polypeptide described above.

Thus according to this aspect of the present invention, expression of the polypeptide chimera is directed by a tumor specific element, such as, but not limited to, the gastrin-releasing peptide (GRP) promoter [AF293321S3; Morimoto E Anticancer Res 2001 January-February;21(1A):329-31], the hTERT promoter [AH007699; Gu J, Gene Ther 2002 January;9(1):30-7], the Hexokinase type II promoter [AF148512; Katabi M M, Hum Gene Ther. 199]Jan. 20;10 (2):155-64.], or the L-plastin promoter [L05490, AH002870, MMU82611; Peng X Y, Cancer Res. 2001 Jun. 1;61(11): 4405-13].

Expression of the polypeptide chimera (e.g., Fas-c) in tumor cells activates apoptosis in these cells and thus leads to cell death, which in turn causes tumor growth slowdown or arrest, and possibly tumor shrinkage.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion. Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., Molecular Cloning—A Laboratory Manual, Cold Spring Harbor Laboratory, Cold Spring Harbor, N.Y. (1989). The manual is hereinafter referred to as "Sambrook". Other general references are provided throughout this document. The procedures therein are believed to be well known in the art and are provided for the convenience of the reader. All the information contained therein is incorporated herein by reference.

Example 1

In-vitro Assay for Pro-apoptotic Gene Activity in Endothelial Cells (BAEC) and 293 Cells In cancer treatment, anti-angiogenic therapy targets the evolving vasculature which nourishes the growing tumor [Folkman J. N Engl J Med (1995) 333(26):1757-63]. As the research of apoptosis, or programmed cell death, has progressed, numerous genes that encode selective and efficient cell death regulators have been identified [Strasser et al. Annu Rev Biochem (2000) 69:217-45.].

The present study screened several pro-apoptotic genes in order to identify an agent most suitable for anti-angiogenic therapy. Several pro-apoptotic genes including MORT1 (FADD—Fas associated death domain protein, GenBank Accession number NM_003824), RIP (receptor-interacting-protein, GenBank Accession number U25995), CASH (c-FLIP, GenBank Accession number AF010127), MACH (caspase 8 GenBank Accession number X98172), CPP32 (caspase 3, GenBank Accession number U13737), caspase ](U60521) and Fas-chimera (Fas-c), a previously described fusion of two "death receptors", constructed from the extracellular region of TNFR1 and the trans-membrane and intracellular regions of Fas [Boldin M P et al. J Biol Chem (1995) 270(14):7795-8, see FIG. 1a) were PCR amplified and cloned into the pcDNA3 (Invitrogen, Inc.) mammalian expression vector using well known prior art cloning techniques.

Figure 4:
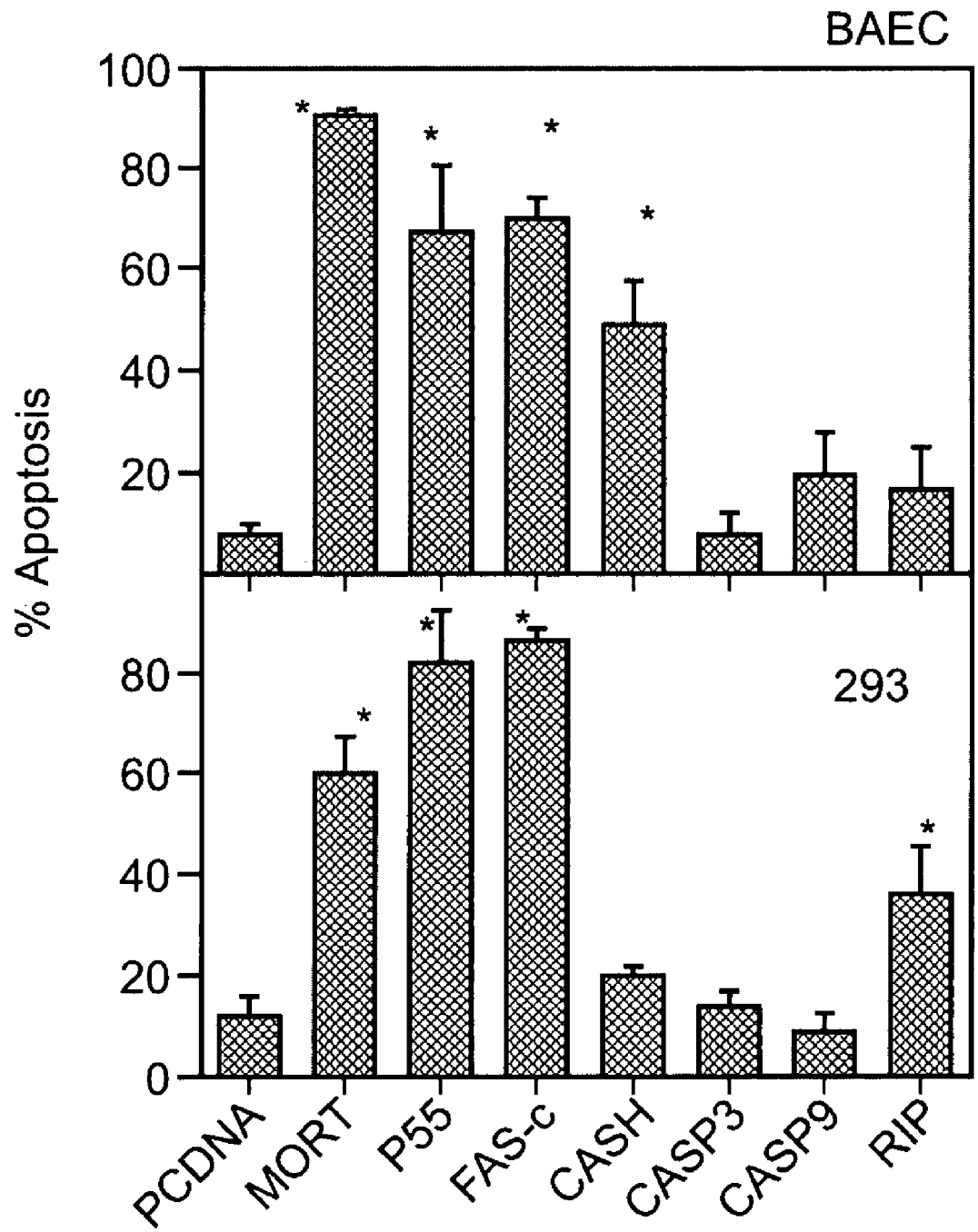
FIG. 4 are histograms quantifying apoptotic activity of the indicated pro-apoptotic genes in transfected BAEC and 293 cells.

These pro-apoptotic gene constructs were co-expressed along with pGFP in BAEC (Bovine Aortic Endothelial Cells) and 293 cells, which were used as non-endothelial control cells. 24 hours post transfection, cells were analyzed using fluorescent microscopy. Apoptotic cells were identified based on typical morphology, (i.e., small and round shape) using fluorescence microscopy (FIGS. 2*a-b*). Further assessment of the apoptotic phenotype was effected using electron microscopy (FIGS. 3*a-f*). Quantification of the apoptotic effect showed that MORT1, TNFR1 and Fas-chimera induced the highest apoptotic activity in BAEC and 293 cells (FIG. 4*a-b*). Caspase 3 and ]were less potent in this respect, probably because they were in an inactive zymogen form. Based on these results, the Fas-chimera (Fas-c) gene was selected for the generation of an adenoviral-vector to be used in anti-angiogenic therapy.

Example 2

Figure 1B:
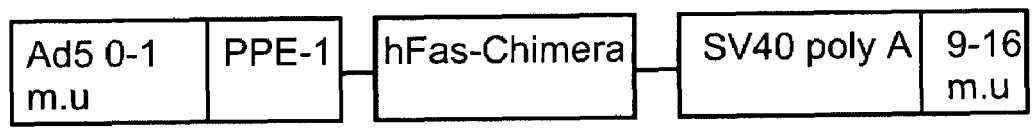
Figure 1B:
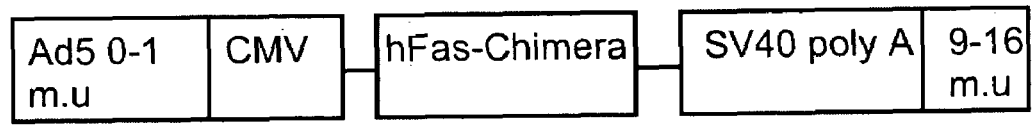

Production of Recombinant Adenoviruses Encoding Fas-chimera Under the Control of the Modified PPE-1 Promoter A cDNA encoding a full length Fas-chimera was subcloned into the plasmid pPACPPE1-3x containing the modified pre-proendothelin1 promoter (see FIG. 1*b*). Recombinant adenoviruses were produced by co-transfection of this plasmid with pJM17 plasmid into human embryonic kidney 293 cells. Successful viral cloning was verified via PCR amplification (FIG. 5*a*).

In order to determine the expression of Fas-c in the target cells, endothelial BAEC cells were transduced with the indicated titer of Ad-PPE-Fas-c. 72 h post transduction cells were lysed and cellular proteins resolved using a non-reducing SDS-PAGE gel. Western blot analysis was performed using anti-TNFR1 antibody (Sc-7895, Santa-Cruz Biotech). As demonstrated in FIG. 5*b*, a prominent band migrating at 45 kD was clearly evident and its expression was dose-dependent, suggesting correct folding and expression of the chimeric protein. In contrast, no corresponding bands were evident in non-transduced endothelial cells or in cells transduced with control empty viral vector. Thus, these results confirmed that the adenoviral-mediated gene transfer of Fas-c results in transgene expression in the target cells.

Example 3

Ad-PPE-Fas-c Expression Induces Apoptosis in Endothelial Cells

Figure 6C:
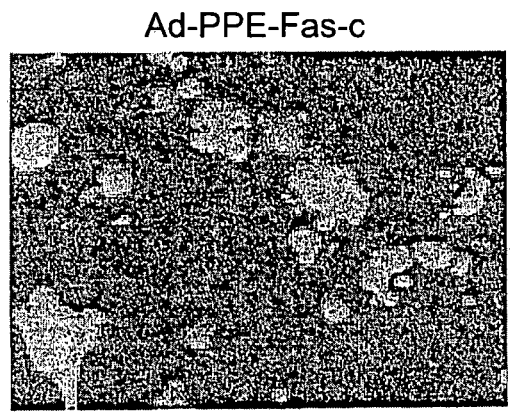

The ability of Ad-PPE-Fas chimera to induce apoptosis of endothelial cells was determined. As shown in FIGS. 6*a-b*, pre-proendothelin directed, adenovirus-mediated transduction of endothelial cells resulted in an evident and massive cell death; HUVEC and BAEC infected with Ad-PPE-Fas-c ($10^3$ MOI) had morphological features of adherent cells undergoing apoptosis including membrane blebbing, rounding and shrinking and detachment from the culture dish. In contrast, cells infected with control viruses at the same MOI, maintained normal appearance and growth rate. Cells transduced with 100 MOI presented only a minimal degree of cell death (data not shown).

Figure 6D:
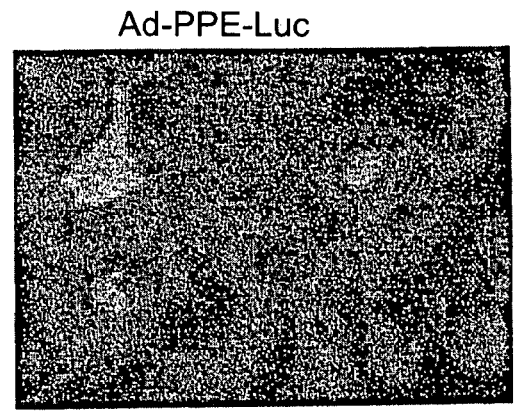

Further assessment of the cytotoxic properties of Ad-PPE-Fas-c was effected by expressing this virus in cells expressing the reporter gene GFP under the control of the PPE-1 promoter. As is evident from FIGS. 6*c-d*, most of the transduced cells acquired a typical apoptotic appearance 72 hours following transduction, whereas cells co-transduced with control virus and Ad-PPE-GFP appeared normal.

Figure 7:
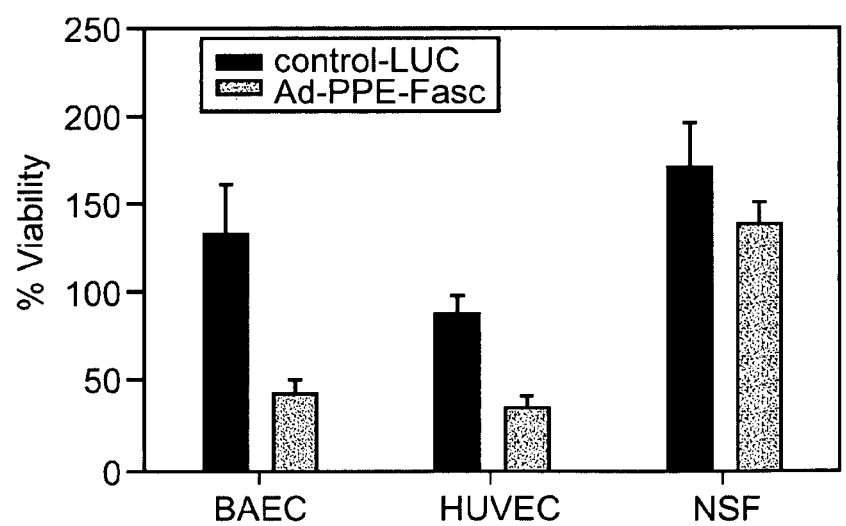
FIG. 7 is a histogram illustrating apoptotic specific effect of Ad-PPE-1-3x-Fas-chimera on endothelial cells. Viability of endothelial (BAEC, HUVEC) and non-endothelial (Normal skin fibroblasts-NSF) cells was quantified by crystal violet staining 72 h post infection with either Ad-PPE-1-3x-Fas-chimera or control (luciferase) virus.

The cytotoxic effect of Fas-c was quantified using crystal violet staining. As shown in FIG. 7, infection of BAEC and HUVEC with Ad-PPE-Fas-c resulted in mortality rates of 57% and 65%, respectively, while the control virus did not affect cell viability.

The endothelial cell specificity of the pro-apoptotic vector Ad-PPE-Fas—was demonstrated by infecting NSF (normal skin fibroblasts) with this vector. These cells, which express low levels of PPE-1 [Varda-Bloom, N. et al. Gene Ther 8, 819-27. (2001)] were not affected by infection with Ad-PPE-Fas-c. In contrast, the recombinant vector Ad-CMV-Fas-c induced apoptotic in these cells.

Example 4

Figure 8:
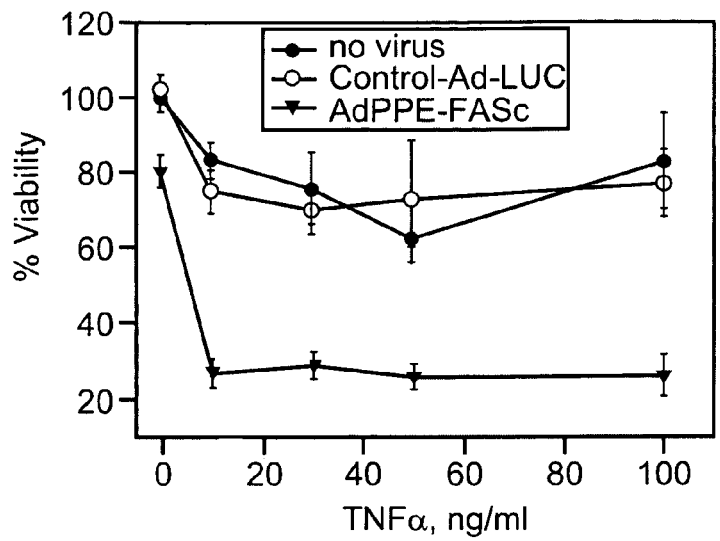
FIG. 8 shows a dose response effect of TNFα administration on Fas-chimera mediated apoptosis. BAEC were infected with Ad-PPE-1-3x-Fas-c. 48 h post infection TNF was added to the growth medium (at the indicated dose). Viability was determined by the crystal violet assay 24 h thereafter.
Figure 9A:
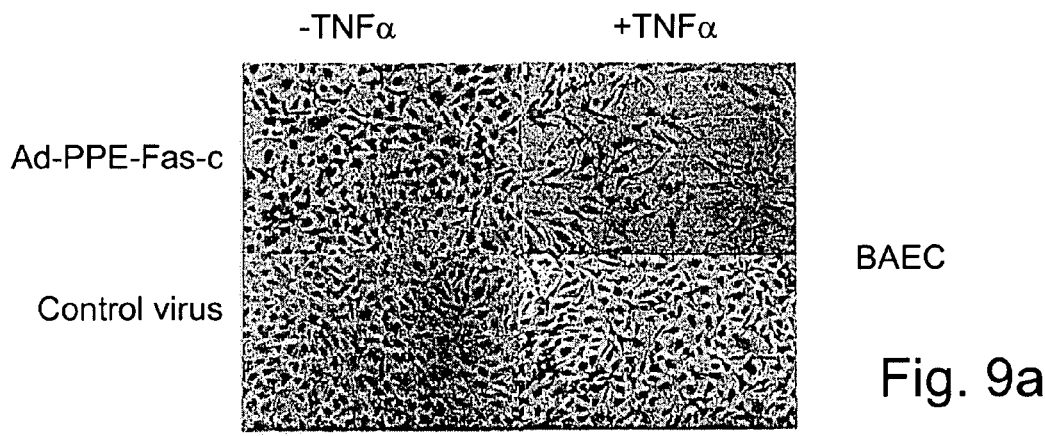
FIGS. 9a-e are photomicrographs illustrating an endothelial cell-specific apoptosis mediated by the cooperative action of TNFα ligand and Fas-c receptor. The indicated cells were incubated in the presence or absence of TNFα (10 ng/ml) 48 h following infection with Ad-PPE-1-3x-Fas-c; crystal violet staining was effected 72 h post infection.
Figure 9B:
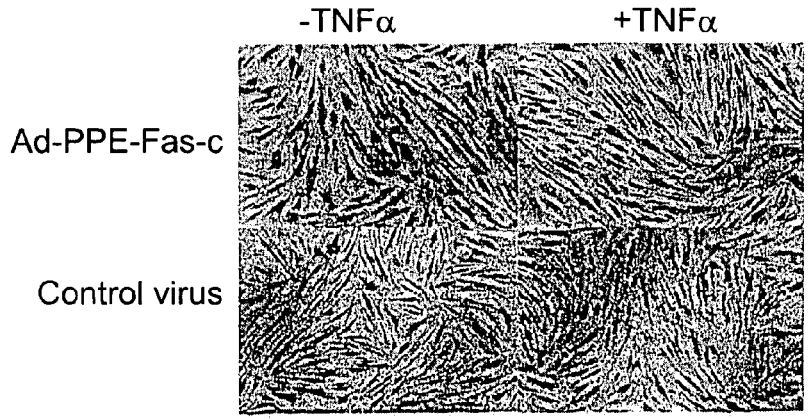
Figure 9C:
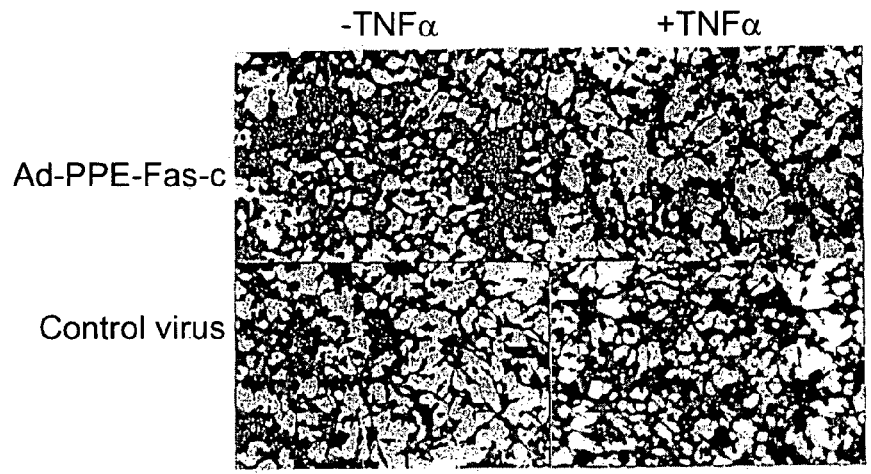
Figure 9D:
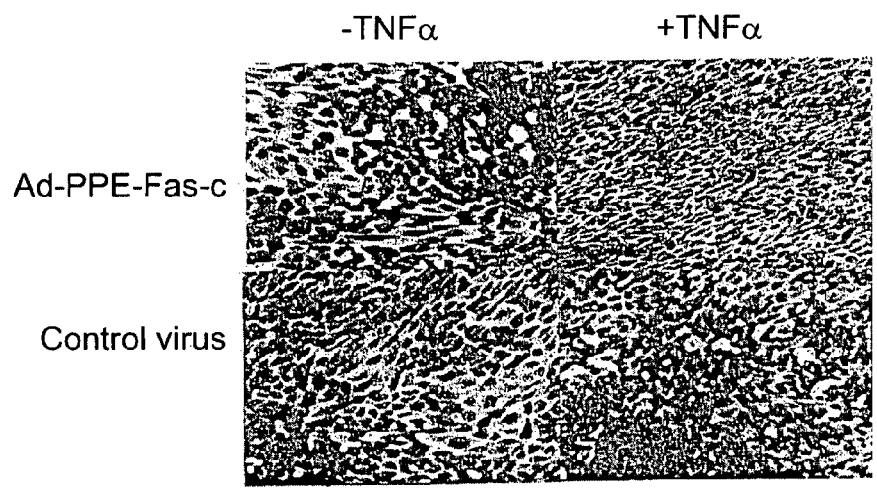
Figure 9E:
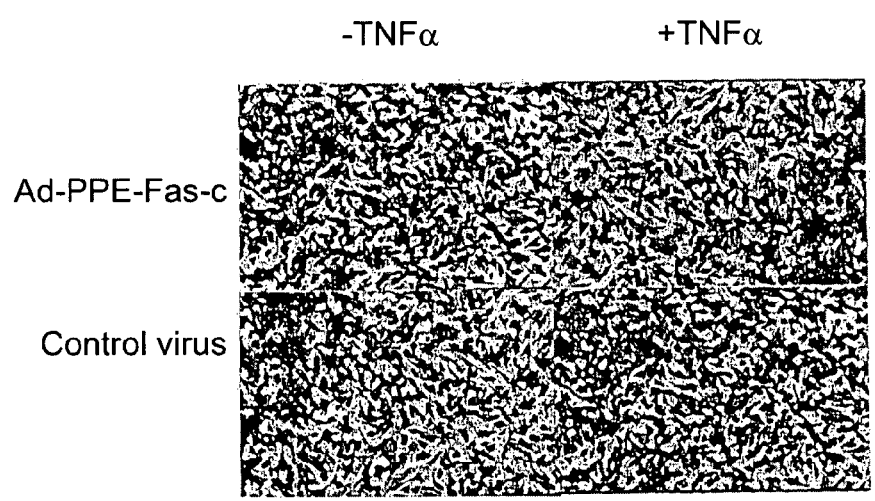

Co-administration of Ad-PPE-Fas-c Receptor and TNFα Ligand Augments the Pro-apoptotic Effect in a Selective Manner The ability of TNFα to augment the apoptotic effect in Fas-c expressing cells was investigated. Human TNFα was added to an endothelial cell culture 48 h-post virus infection with Ad-PPE-Fas-c (MOI of 100). Cell viability was assayed 24 h later. As shown in FIG. 8, TNFα (10 ng/ml) induced a 73% decrease in viabilty of Ad-PPE-Fas-c infected cells, whereas no significant mortality was effected by TNFα alone or in cells infected with control virus (Ad-Luc).

Figure 10A:
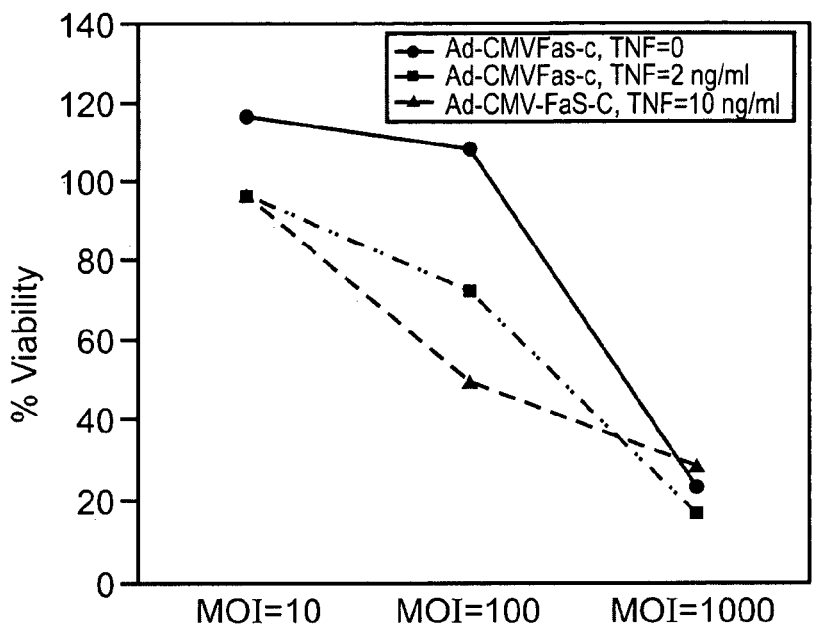
FIG. 10a is a dose response curve illustrating the TNFα-dependent apoptotic effect of Ad-CMV-Fas-c on endothelial cells. Viability of BAEC cells infected with the indicated MOI of Ad-CMV-Fas-chimera was determined following incubation with TNFα.

To substantiate the effect of TNFα, cell specificity was addressed. NSF (normal skin fibroblasts), DA3 (mouse mammary adenocarcinoma), D122 (Lewis lung carcinoma) and B16 melanoma cells were infected with Ad-PPE-Fas-c or a control virus. 48 hours later, culture was supplemented with TNFα and cell morphology was assessed following staining with crystal violet. As shown in FIGS. 9*a-e*, non-endothelial cells infected with Ad-PPE-Fas-c displayed normal appearance and were not affected by TNF. On the other hand, adenoviral mediated infection of BAEC with Fas-c resulted in marked decrease in cell viability when TNF was added. The non-selective apoptotic activity of Fas-c driven by CMV promoter is demonstrated in FIG. 10*a* which illustrates the TNF-dependent apoptotic effect of Ad-CMV-Fas-c on endothelial cells. Viability of BAEC cells infected with the indicated MOI of Ad-CMV-Fas-chimera was determined following incubation with TNF.

Figures 10B, 10C, 10D:
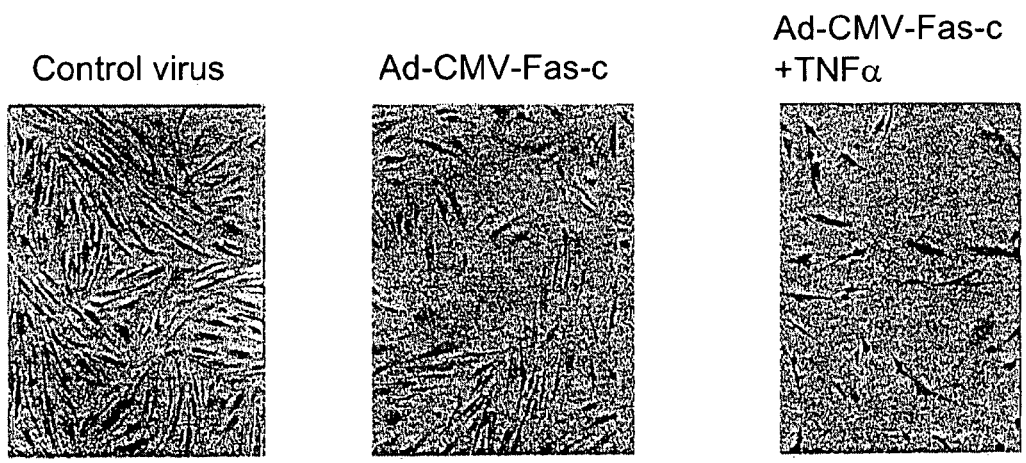
FIGS. 10b-d illustrate the apoptotic effect of TNFα ligand and Ad-CMV-Fas-chimera on the non-endothelial cells NSF.

Notably, the non-endothelial-specific vector Ad-CMV-Fas-c caused TNFα-dependent apoptosis of both endothelial and non-endothelial cells (FIGS. 10*b-d*).

Example 5

Ad-PPE1-Fas-c Induces In-vivo Growth Retardation of B16 Melanoma in Mice

The B16 melanoma mouse model was used in order to test the anti-tumoral effect of Fas-c expressed from the PPE1-3x promoter. B16 melanoma cells ($8 \times 10^5$) were injected subcutaneously to the flank region of 40 C57bl/6 mice. When the tumor was palpable ($\approx 5 \times 5$ mm), the mice were randomized into 4 groups as follows: (i) control-saline injection; (ii) control virus (Adeno virus containing luciferase controlled by PPE promoter); (iii) Ad-PPE1-3x-Fas-c-virus containing the Fas-TNF receptor chimeric gene controlled by the preproendothelin (PPE) promoter; and (iv) Ad-CMV-Fas-c-virus containing the Fas-TNF receptor chimeric gene controlled by the non-endothelial specific, CMV promoter.

Figure 11A:
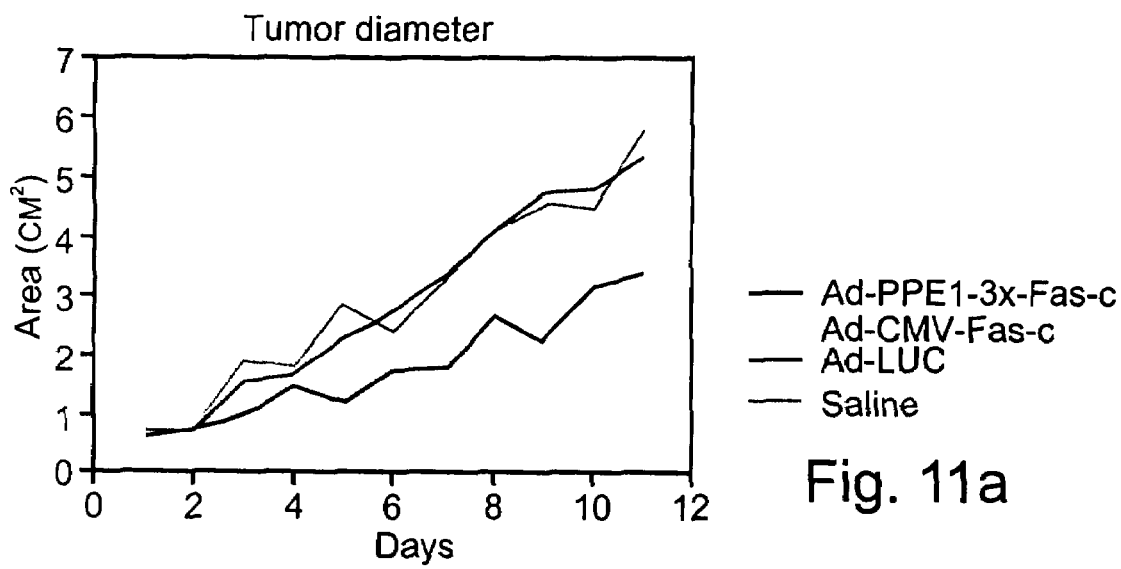
FIGS. 11a-c illustrate the In-vivo anti-tumoral effect of Ad-PPE-1-3x-Fas-c. Mice inoculated with B16 melanoma cells were injected intravenously with Ad-PPE-1-3x-Fas-c, Ad-CMV-Fas-chimera, control virus or saline when tumor was palpable.
Figure 11B:
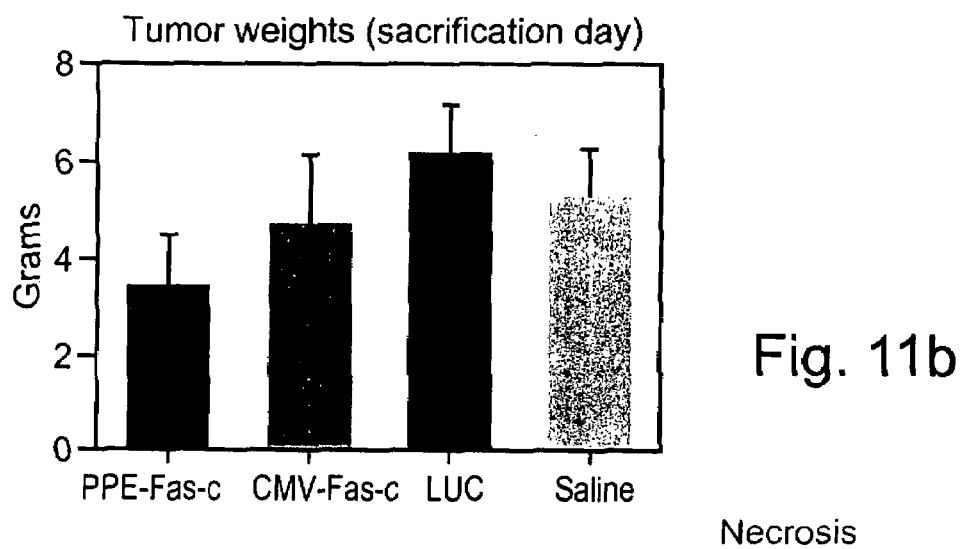
Figure 11C:
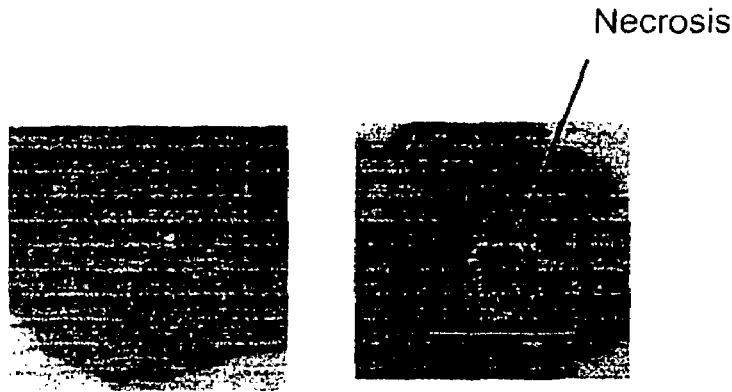

Tumor size (length and width) was measured using a hand caliper. As shown in FIG. 11*a*, tumor size was lower for mice treated with Ad-PPE1-3x-Fas-c or Ad-CMV-Fas-c as compared to control mice. Tumor weights at the end of the treatment period was also lower in the Ad-PPE1-3x-Fas-c treated mice (FIG. 11*b*). Mice injected with Ad-PPE1-3x-Fas-c showed marked necrosis of their tumor (FIG. 11*c*).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A nucleic acid construct comprising:
   (a) a first polynucleotide region encoding a chimeric polypeptide which comprises a TNF Receptor 1 (TNFR1) ligand binding domain fused to a Fas effector domain; and
   (b) a second polynucleotide region which comprises a pre-pro endothelin (PPE)-I-3X promoter for directing expression of said chimeric polypeptide, wherein the promoter is operably linked to the polynucleotide of a).

2. An isolated mammalian cell transformed with the nucleic acid construct of claim 1.

3. A pharmaceutical composition comprising a pharmaceutically acceptable carrier and a nucleic acid construct, wherein said nucleic acid construct comprises:
   (a) a first polynucleotide region encoding a chimeric polypeptide comprising a TNF Receptor 1 (TNFR1) ligand binding domain fused to a Fas effector domain; and
   (b) a second polynucleotide region which comprises a pre-pro endothelin (PPE)-I-3X promoter for directing expression of said chimeric polypeptide, wherein the promoter is operably linked to the polynucleotide of a).

4. The nucleic acid construct of claim 1, wherein the nucleic acid construct is inserted in an adenoviral vector.

5. The pharmaceutical composition of claim 3, wherein said nucleic acid construct is inserted in an adenoviral vector.

* * * * *